United States Patent
Egilsson et al.

(10) Patent No.: US 9,629,732 B2
(45) Date of Patent: *Apr. 25, 2017

(54) LINER FOR PROSTHETIC AND ORTHOPEDIC SYSTEMS

(71) Applicant: OSSUR HF, Reykjavik (IS)

(72) Inventors: Egill Sveinbjorn Egilsson, Reykjavik (IS); Palmar I. Gudnason, Mosfellsbaer (IS); Olafur Freyr Halldorsson, Reykjavik (IS); Thordur Elefsen, Mosfellsbaer (IS)

(73) Assignee: OSSUR HF, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 14/729,862

(22) Filed: Jun. 3, 2015

(65) Prior Publication Data
US 2015/0265431 A1    Sep. 24, 2015

Related U.S. Application Data

(63) Continuation of application No. 13/611,811, filed on Sep. 12, 2012, now Pat. No. 9,050,201, which is a
(Continued)

(51) Int. Cl.
*A61F 2/78* (2006.01)
*A61F 2/80* (2006.01)
(Continued)

(52) U.S. Cl.
CPC ............ *A61F 2/7812* (2013.01); *A61L 27/26* (2013.01); *A61L 27/56* (2013.01);
(Continued)

(58) Field of Classification Search
CPC ............ A61F 2/7812; A61F 2002/7818; A61F 2002/785
(Continued)

(56) References Cited

U.S. PATENT DOCUMENTS

RE2,218 E    4/1866  Mennel
1,066,605 A  7/1913  Hanger
(Continued)

FOREIGN PATENT DOCUMENTS

AU    35864/89 A    12/1989
EP    0 346 697 A2  12/1989
(Continued)

OTHER PUBLICATIONS

Uellendabl, Jack E., "Prosthetic Socks and Liners, First Step: A Guide for Adapting to Limb Loss", vol. 2, 2001, 4 pages. Retrieved from the Internet Jul. 12, 2007; http://www.amputee-coalition.org/first-step/firststepv2-s2a09.html.

*Primary Examiner* — David H Willse
*Assistant Examiner* — Javier Blanco
(74) *Attorney, Agent, or Firm* — Workman Nydegger

(57) ABSTRACT

A liner is arranged for use in prosthetic and orthopedic devices. The liner defines first and second end portions, and inner and outer surfaces. The liner includes an inner layer having a frictional component and forms at least part of the periphery of the inner liner surface. The inner layer defines a plurality of apertures. A porous element is in communication with the inner liner surface and is connected to the inner layer such that the apertures permit a transfer of air from the inner surface to the porous element. A base layer adjoins the porous element and extends between the first and second end portions of the liner.

14 Claims, 7 Drawing Sheets

Related U.S. Application Data continuation of application No. 12/219,953, filed on Jul. 31, 2008, now Pat. No. 8,308,817.

(60) Provisional application No. 60/935,261, filed on Aug. 2, 2007.

(51) Int. Cl.
*A61L 27/26* (2006.01)
*A61L 27/56* (2006.01)
*A61F 2/30* (2006.01)
*A61F 2/50* (2006.01)

(52) U.S. Cl.
CPC ........... *A61F 2002/30024* (2013.01); *A61F 2002/5055* (2013.01); *A61F 2002/5056* (2013.01); *A61F 2002/785* (2013.01); *A61F 2002/7818* (2013.01); *A61F 2210/0076* (2013.01); *A61F 2250/0021* (2013.01); *A61F 2250/0023* (2013.01)

(58) Field of Classification Search
USPC .......................................................... 623/36
See application file for complete search history.

(56) References Cited

U.S. PATENT DOCUMENTS

| | | |
|---|---|---|
| 1,366,027 A | 1/1921 | Savastano |
| 2,267,070 A | 12/1941 | Baldwin |
| 3,451,232 A | 6/1969 | Belzidsky |
| 3,600,717 A | 8/1971 | McKeehan |
| 3,892,239 A | 7/1975 | Masso Remiro |
| 3,983,870 A | 10/1976 | Herbert et al. |
| 4,308,862 A | 1/1982 | Kalmar |
| 4,387,710 A | 6/1983 | Beatty, III |
| 4,479,272 A | 10/1984 | Beldzisky |
| 4,635,626 A | 1/1987 | Lerman |
| 4,813,090 A | 3/1989 | Ibrahim |
| 5,156,629 A | 10/1992 | Shane et al. |
| 5,163,965 A | 11/1992 | Rasmusson et al. |
| 5,728,169 A | 3/1998 | Norvell |
| 5,888,231 A | 3/1999 | Sandvig et al. |
| 5,972,036 A | 10/1999 | Kristinsson et al. |
| 6,123,716 A | 9/2000 | Augustine et al. |
| 6,136,039 A | 10/2000 | Kristinsson et al. |
| 6,544,292 B1 | 4/2003 | Laghi |
| 6,592,539 B1 | 7/2003 | Einarsson et al. |
| 6,654,960 B2 | 12/2003 | Cho |
| 6,706,364 B2 | 3/2004 | Janusson et al. |
| 6,923,834 B2 | 8/2005 | Karason |
| 6,974,484 B2 | 12/2005 | Caspers |
| 7,025,793 B2 | 4/2006 | Egilsson |
| 7,090,651 B2 | 8/2006 | Chiang et al. |
| 7,118,602 B2 | 10/2006 | Bjarnason |
| 7,488,349 B2 | 2/2009 | Einarsson |
| 7,762,973 B2 | 7/2010 | Einarsson et al. |
| 7,896,827 B2 | 3/2011 | Ingimundarson et al. |
| 7,909,884 B2 | 3/2011 | Egilsson et al. |
| 2005/0149202 A1 | 7/2005 | Schaffer et al. |
| 2006/0135902 A1 | 6/2006 | Ingimundarson et al. |
| 2007/0005149 A1 | 1/2007 | Egilsson et al. |
| 2007/0055383 A1 | 3/2007 | King |
| 2007/0185425 A1 | 8/2007 | Einarsson et al. |
| 2007/0225824 A1 | 9/2007 | Einarsson |

FOREIGN PATENT DOCUMENTS

| | | |
|---|---|---|
| JP | 2004-160052 A | 6/2004 |
| WO | 01/67842 A1 | 9/2001 |
| WO | 2006/015599 A1 | 2/2006 |
| WO | 2007/111971 A2 | 10/2007 |

LINER FOR PROSTHETIC AND ORTHOPEDIC SYSTEMS

FIELD OF THE INVENTION

The present invention relates generally to a liner for prosthetic and orthopedic devices. More specifically, the liner is adapted to provide an improved interface in a prosthetic or orthopedic system between a limb and another prosthetic or orthopedic device via management of perspiration occurring along the limb, prevention of slippage of the limb and cushioning of the limb.

BACKGROUND

Numerous liners or padding are employed in prosthetic and orthopedic systems, and serve as an interface between a corresponding prosthetic or orthopedic device and a limb.

By way of example, in the field of prosthetic devices, a liner sleeve is generally understood as a sleeve worn over a post-operative stump or limb that serves as the interface between the limb and a prosthesis or a prosthetic device, such as a hard socket. Liners are typically made of an air impermeable elastomer material, such as silicone. Liners may comprise a single layer or multiple layers, with different layers providing different benefits to the wearer.

Liners are used traditionally to cushion a post-operative stump or limb with respect to a prosthesis that is installed over the limb and coupled to the sleeve by a conventional locking mechanism. The thickness of the liner may be increased to provide additional cushioning between the limb and the prosthesis, thereby increasing comfort to the user.

In addition to providing cushioning, the liner also serves to protect the limb from irritation that might be caused by movement of the prosthesis against the limb. In the absence of a liner, the prosthesis will directly contact the skin. Any movement or slippage of the prosthesis at the interface with the limb will therefore result in friction between the prosthesis and limb and, consequently, irritation to the limb. Presence of the liner between the limb and the prosthesis eliminates this problem by serving as a protective barrier between the limb and the prosthesis. In other words, movement at the interface with the limb will be borne by the liner and not the limb.

Of course, in order for the liner to protect the limb from irritation caused by movement of the prosthesis at the interface between the prosthesis and the limb, the liner preferably does not slip on the limb. That is to say, if the liner is capable of slipping on the limb, then the limb may become irritated by the friction caused by the liner rubbing against the skin of the limb.

Traditionally, liners have addressed this issue by utilizing a liner having a tacky surface for the surface that comes into direct contact with the skin of the limb. The tacky inner surface of the liner ensures the liner does not slip or rub against the skin of the limb. The liner stays firmly in place against the limb, even when external forces such as movement of the prosthesis against the external surface of the liner are acting on the liner.

The tacky inner surface of a liner does not always prevent slippage of the liner against the limb. Specifically, when the liner is made from a non-absorbent elastomer material, perspiration build-up in the liner tends to cause the liner to lose suspension. The equal pressure applied to the limb by the liner results in a thin film of perspiration forming and distributing throughout the liner. The thin film of perspiration forms an essentially frictionless gap between the limb and the liner, thus allowing the liner to easily slide on the limb. With no means to escape, the thin film of perspiration builds up between the limb and slippage of the liner is more likely to occur.

Liners find a variety of applications also in orthopedic devices for providing an interface to the limb. Such liners may be used alone in reinforcing a limb, or may include reinforcing elements or be used in combination with braces for a variety of anatomical portions.

It is therefore one of the objects of the embodiments described herein to create an improved liner that effectively manages perspiration formed by a limb, prevents slippage of the liner on the limb, and further provide suitable cushioning for the limb. Such a liner can be used in a variety of applications for both prosthetic and orthopedic systems in combination with prosthetic and orthopedic devices.

SUMMARY

The present invention is directed, at least in part, to embodiments of a liner for prosthetic and orthopedic systems designed to effectively manage perspiration formed by a limb, prevent slippage of the liner on limb, and further provide suitable cushioning for a limb. In the exemplary embodiments described herein, they are discussed and shown within the context of a liner in a prosthetic system and in combination with a residual limb and a hard socket. However, the liner of the invention is not limited to such a prosthetic environment, and instead embraces any application requiring perspiration management, prevention of slippage, or cushioning of the limb.

According to one embodiment, the liner comprises an elongate, generally porous layer and a perforated inner layer located on the inner surface of the porous layer. The perforated inner layer conforms to the shape of the porous layer, thus forming a two-layer liner, with the limb contacting the perforated inner layer.

The porous layer of the liner may be a three-dimensional woven synthetic material. The three-dimensional material includes interconnected gaps and tunnels running throughout the material, thereby allowing for the transport of liquid from one surface of the porous layer to the other.

In one variation of the embodiment, the liner further comprises an outer layer located on the outer surface of the porous layer. Like the perforated inner layer located on the porous layer, the outer layer conforms to the shape of the porous layer. The outer layer is capable of providing additional beneficial characteristics, such as adding support to the shape of the liner.

According to one configuration of the embodiment, at least one of the outer layer and the perforated inner layer is made from a polymer material. More specifically, the outer layer and inner layer are each constructed from silicone. Such materials can provide additional desirable characteristics to the liner, including structural support and cushioning.

The perforated inner layer may have a tacky inner surface for contacting the skin of the limb. The tacky surface provides a safeguard against the liner slipping on the limb.

In one construction of the embodiment, the holes in the perforated inner layer are larger than the pores of the porous layer. Such a configuration provides large spaces for perspiration formed by the limb to collect and then move into the smaller pores of the porous layer. The large holes also decrease the area of the inner layer contacting the skin of the limb, and thereby reduce the opportunity for perspiration to collect between the limb and the inner layer.

The thickness of the porous layer may also be greater than the thickness of the perforated inner layer and the outer layer in order to dedicate more of the total thickness of the liner to providing space and areas for the perspiration to travel away from the limb.

In another variation of the embodiment, the outer layer is water permeable and the perforated inner layer is water impermeable. Such a configuration encourages perspiration formed at the limb to be drawn towards the holes in the perforated inner layer and into the porous layer. This variation also provides a means of escape from the liner for the perspiration once it has traveled through the porous layer and reached the outer layer.

Further, it is also possible to form the outer layer only in the distal area of the liner. In this configuration, perspiration traveling through the porous layer will not be trapped at the outer surface of the porous layer, while an attachment member for attaching a prosthesis may be attached on the outer layer at the distal area of the liner.

When an attachment member is located on the liner (whether the outer layer is located only in the distal area of the liner or about the entire liner), the means for attachments may include, but are not limited to, a seal-in suspension, a locking pin, a vacuum with sleeve, hook-and-loop fasteners, adhesions, or any other suitable means known to the skilled person.

In another embodiment described herein, the liner comprises an elongate base layer having a plurality of holes formed therein. The liner further includes porous members filled in each of the holes in the base layer and a perforated inner layer located on the inner surfaces of the base layer and porous members. The porous members provide a means for channeling perspiration formed on the limb through and out of the liner, rather than collecting between the limb and the liner. Because the porous members extend through to the outer surface of the liner, the perspiration traveling through the porous members can exit the liner. Further, the perforated inner layer helps to channel the perspiration into the porous members.

In another configuration of the embodiment, the porous members are three-dimensional woven synthetic material. The three-dimensional structure provides interconnected gaps and tunnels through which the perspiration can travel. The gaps and tunnels of the three-dimensional woven synthetic material run through the entirety of the material, thereby providing a means for the perspiration to exit the liner.

The base layer and perforated inner layer may be made from a polymeric based material, such as silicone. The polymeric materials are able to provide additional benefits to the liner, such as cushioning and support.

In one variation of the embodiment, the inner surface of the perforated inner layer may be tacky. The tacky surface provides friction between the liner and the limb, and further prevents slippage of the liner on the limb. In addition, the perforations of the perforated inner layer may be larger than the pores of the porous layer such that the perspiration formed by the limb will be more likely to collect in the perforations of the inner liner and move into the porous members. This configuration also minimizes the surface area where perspiration may collect between the inner layer and the limb. Using a water impermeable material for the perforated inner layer also tends to help channel perspiration towards the porous members.

In another configuration of the embodiment, the holes in the base layer are located between the distal and proximal areas of the base layer. When the distal area is free of holes with porous members formed therein, the distal area is better suited for supporting a prosthesis attachment member. Such a prosthesis attachment member located in the distal area of the liner may include a seal-in suspension, a locking pin and a vacuum with sleeve.

In another embodiment described herein, the liner comprises an elongate porous polymer foam layer and a porous silicone layer coated on both the inner and outer surfaces of the polymer foam layer. The porous polymer foam is absorbent and therefore perspiration from the limb may pass through the inner porous silicone coating and perspiration will absorb into the porous foam layer rather than form thin films of perspiration between the liner and the limb.

In a variation of the embodiment, the liner also includes discrete portions of a moisture-absorbing material, such as in the form of a powder, to further aid in the absorption of perspiration. The portions of the moisture-absorbing material may be embedded within the porous polymer foam or may be located on the inner and outer surfaces of the porous polymer foam layer. In a further variation, the discrete portions of moisture-absorbing material are located both within the polymer foam and on the inner and outer surfaces of the porous polymer foam layer.

It will be noted that discrete portions of a moisture-absorbing material may be provided in any of the types of porous layers described herein such as by impregnating, embedding, meshing or injecting such discrete portions of moisture absorbing material in the porous layer.

In one construction, the porous polymer foam is porous silicone foam. The silicone foam may further include a plurality of hydrophilic particles anchored to the pore walls of the foam.

The liner of the embodiment may include additional layers, such as an outer layer formed on the outer surface of the outer coating of silicone. Such layers are capable of providing additional characteristics to the liner, such as support to keep the shape of the liner. The outer layer may be formed of porous or non-porous silicone.

In still a further embodiment described herein, the liner comprises a polymer construct wherein the construct is made from multiple layers of polymer threads. The layers of threads create gaps between which perspiration from the limb may travel away from the limb and out of the liner.

In one variation of this embodiment, the polymer threads have a generally rod-like shape. This configuration for the polymer threads helps to ensure that adjacent threads do not block gaps or tunnels in which the perspiration is traveling.

The polymer threads within a single layer may be aligned in parallel. That is to say, the polymer threads of a layer have an organized structure whereby adjacent threads within the layer are parallel. Similarly, adjacent layers of polymer threads are aligned in parallel when stacked upon each other.

With respect to the orientation of polymer threads of different layers, the polymer threads of one layer are not aligned in parallel to polymer threads in an adjacent layer. The polymer threads of a first layer may be aligned at a 45 degree angle to polymer threads in an adjacent layer, or any other angle that creates gaps and tunnels in which perspiration may travel away from the limb.

In yet another embodiment described herein, the liner comprises a conical polymer construct, wherein the polymer construct is made of multiple layers of packed polymer balls. The layers of packed polymer balls create paths in which the perspiration formed on a limb may travel away from the limb. By providing a path for the perspiration to travel away from the limb, the build up of perspiration at the interface of the limb and the liner will be prevented.

In one variation of the embodiment, the polymer balls are packed such that the balls are in contact with adjacent balls. The packed balls configured in this manner will provide a compact liner layer while still providing gaps and tunnels in which the perspiration can travel due to the ball shape. In still another variation of the embodiment, the polymer balls are sphere balls. The polymer balls may also all have the same diameter.

The embodiments described herein may be formed as a close-ended, generally conical sleeve, or may include opposed open ends. Moreover, the liner described herein is not limited tubular type constructions, but is intended to embrace any geometrical configuration having the layer configurations described herein as pertaining to the invention.

Figure 1:
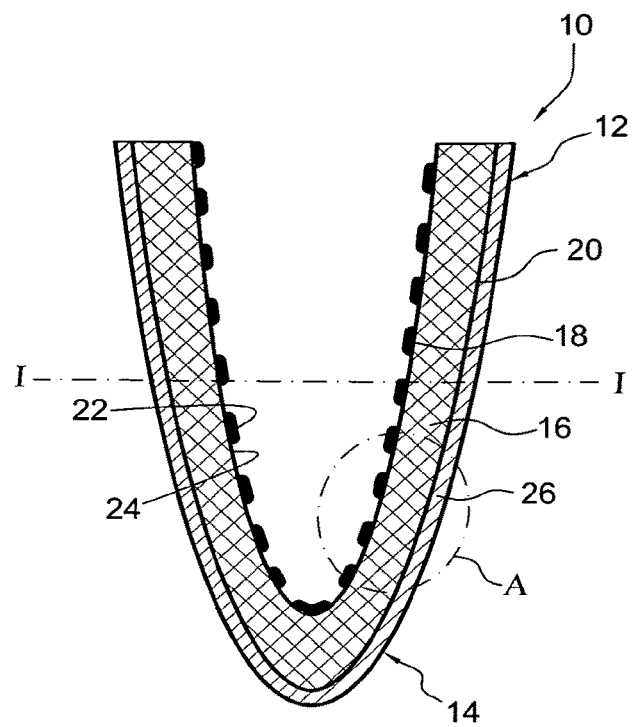
FIG. 1 is a vertical sectional view of an embodiment of a liner.

In the various figures, similar elements are provided with similar reference numbers. It should be noted that the drawing figures are not necessarily drawn to scale, but instead are drawn to provide a better understanding of the components thereof, and are not intended to be limiting in scope, but rather provide exemplary illustrations.

DETAILED DESCRIPTION OF VARIOUS EMBODIMENTS

The embodiments described herein are each adapted to manage perspiration originating from a limb or other anatomical portion of a body while providing superior comfort. In the first and second exemplary embodiments, the liner manages perspiration in part by using porous absorbent layers or members to draw perspiration away from the limb. In the third exemplary embodiment, a porous polymer foam is used to draw perspiration away from the limb. In the fourth and fifth exemplary embodiments, the liners are configured to provide paths and gaps between a series of layers in which perspiration may travel away from the limb.

In the liner embodiments that follow, it will be noted that they are described in the context of a liner sleeve for a limb. However, this context is provided only for exemplary purposes since the liner according to the invention may be arranged in a variety of geometrical configurations for both prosthetic and orthopedic applications. In other words, the configuration of the liner is not limited in construction for use as a liner sleeve in a particular system, and a liner in accordance with the invention may not necessarily be geometrically configured as a close-ended or even open-ended sleeve.

Such alternative configurations include sheets or segments for use in combination with braces, or configured for numerous other prosthetic and orthopedic applications. These sheets or segments may be tailored to correspond to elements of a prosthetic or orthopedic device, such as in a brace, and may be removably mounted for replacement or fixedly secured by known methods to the skilled person.

A. First Embodiment

In a first exemplary embodiment, the liner is formed as an elongate, closed-ended, generally conical shape porous layer wherein a perforated inner layer is located on the inner surface of the porous layer and an outer layer is located on the outer surface of the porous layer.

As shown in FIG. 1, the liner 10 has an elongate, closed-ended, generally conical shape for receiving a limb having roughly the same shape. The liner has a proximal end 12, which is open, and a distal end 14, which is closed.

Figure 2:
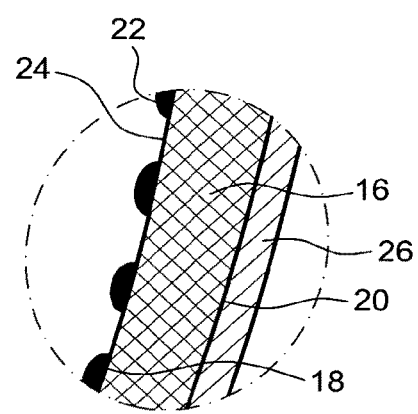
FIG. 2 is a sectional view corresponding to detail A in FIG. 1.
Figure 3:
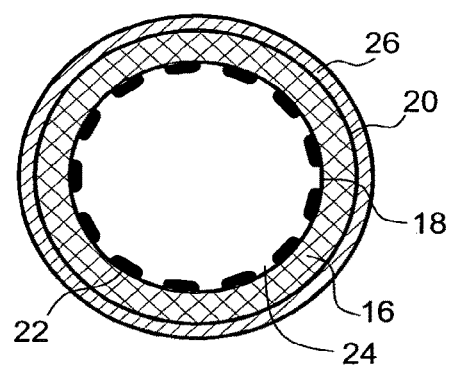
FIG. 3 is a cross-sectional view taken along line I-I in FIG. 1.
Figure 4:
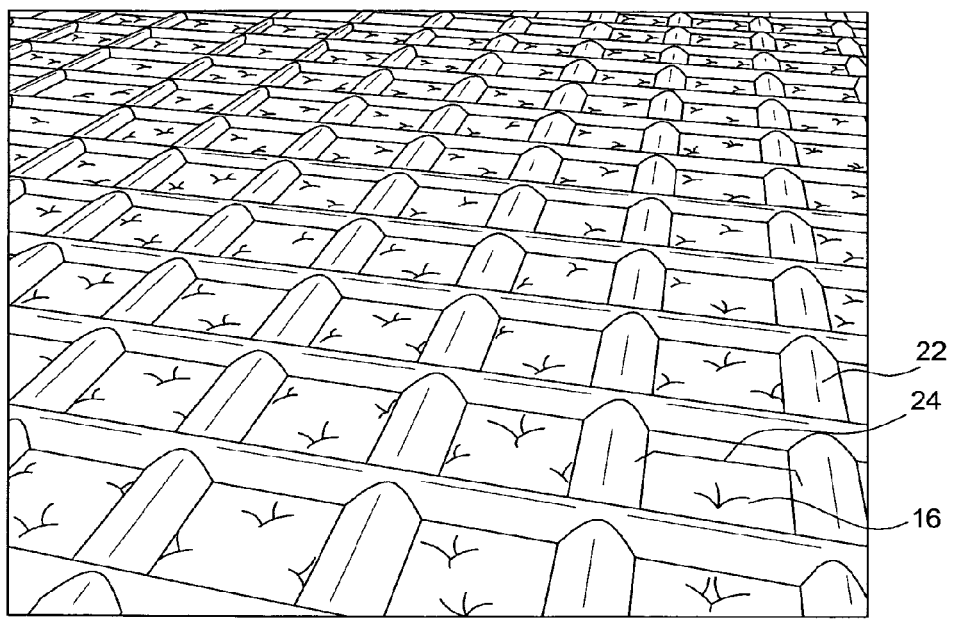
FIG. 4 is a detailed perspective view of the inner surface of the liner depicted in FIG. 1.
Figure 5:
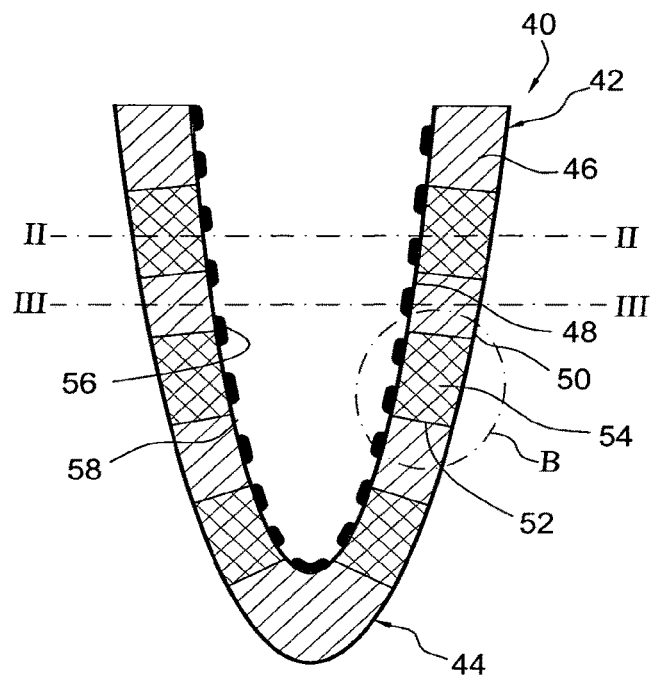
FIG. 5 a vertical sectional view of another embodiment of a liner.
Figure 6:
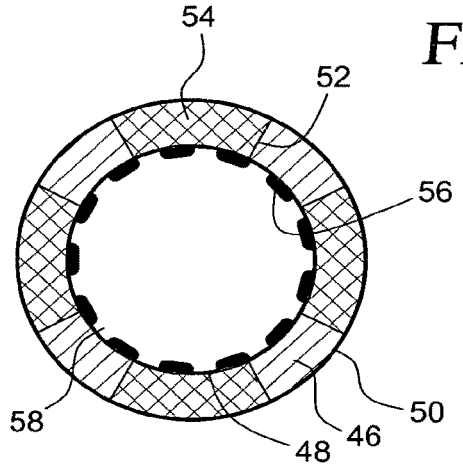
FIG. 6 is a cross-sectional view taken along line II-II in FIG. 5.
Figure 7:
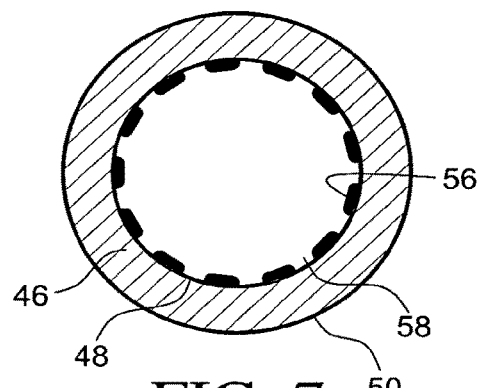
FIG. 7 is a cross-sectional view taken along line III-III in FIG. 5.
Figure 8:
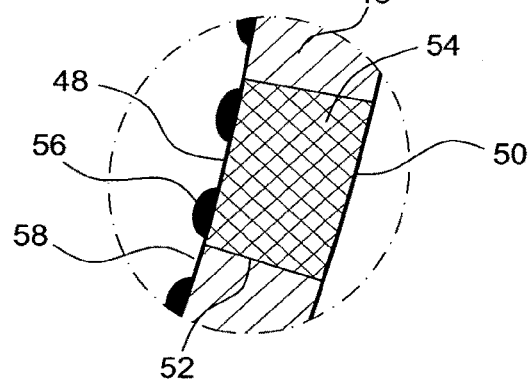
FIG. 8 is a sectional view corresponding to detail B in FIG. 5.

As shown in FIGS. 1, 2 and 3, the liner 10 includes a porous layer 16, a perforated inner layer 18 and an outer layer 20. The porous layer 16 has an inside surface 18 and an outer surface 20 opposing the inner surface 18. On the inner surface 18 of the porous layer 16, an inner layer 22 having perforations 24 is defined. An outer layer 26 is defined on the outer surface 20 of the porous layer 16. The perforated inner layer 22 and the outer layer 26 generally conform to the elongate, conical shape of the porous layer 16, thus forming a tri-layered structure. The layers of the liner may be adhered together by any means known in the art, such as through the use of an adhesive material or by lamination.

Perspiration formed in the areas of skin located over the perforations will be channeled directly to the porous layer, where the perspiration will begin to move through the tunnels and gaps of the porous layer and away from the limb. Perspiration formed in the areas where skin contacts the perforated inner layer will be directed towards the perforations and the porous layer. This is especially the case at the edges of the perforated inner layer where holes are formed and are rounded. The rounded edges allow perspiration to roll down towards the porous layer. Using an impermeable material for the perforated inner layer will also tend to promote the movement of perspiration from the perforated inner layer towards the porous layer.

FIG. 1 depicts the outer layer 26 located co-extensively with the porous layer 16. In other words, the outer layer 26 covers the entire outer surface 20 of the porous layer 16. In an alternate configuration, the outer layer is located in only the distal area 14 of the liner 10. In this manner, any perspiration that travels away from the limb via the porous layer will be able to exit the liner above the distal area since the outside surface of the porous layer is not contained by an outer layer above the distal area. Additionally, the presence of the outer layer in the distal area still allows the outer layer to provide additional beneficial characteristics to the liner, such as supporting the distal area of the liner and also providing a platform on which a prosthesis attachment member may be placed.

The liner may further include a prosthesis attachment member, whether the outer layer is located co-extensively with the porous layer or only in the distal area. Prosthesis attachment mechanisms known in the art may be added to the liner, including, but not limited to, seal-in suspension elements, locking pins and vacuum elements.

The thickness of the liner may be varied depending on such factors such as the amount of cushioning desired by the user. With respect to the thickness of each layer of the liner, the thickness of the layers is limited only by the total thickness of the liner desired.

In one variation of the embodiment, the thickness of the porous layer may be larger than the thickness of the perforated inner layer and the outer layer. The thickness of the porous layer may be greater than the thickness of the perforated inner layer and outer layer such that the porous layer is capable of managing a large amount of perspiration. A porous layer with a greater thickness will have a greater capacity to store perspiration. A larger storage capacity allows the user to wear the liner for a longer period of time without needing to change or clean the liner. Such a configuration makes the liner especially useful when the desired function of the sleeve is to absorb and store perspiration rather than transport it out of the liner.

The overall size of the liner may be any size needed to fit the size of the limb of the user.

The porous layer may be made from any of a number of porous materials capable of absorbing liquid and that are suitable for use in a liner. For example, the porous layer may be a three-dimensional woven synthetic material, wherein the three-dimensional woven structure provides a network of pores, gaps and/or tunnels throughout the material in to which perspiration may travel. The three-dimensional woven structure is also such that these pores, gaps and/or tunnels are interconnected, and provide a path from one surface of the porous layer to the opposing surface. The three-dimensional woven structure may be synthetic in order to increase the durability and longevity of the porous layer as compared to natural materials. However, the porous layer suitable for the embodiment is not limited to synthetic materials where natural materials will achieve common functionality.

A specific example of material suitable for use as the porous material in the liner of the embodiment is made by TYTEX Group, Ikast, Denmark under product designation Quality No. 95289 and Tytex 5754/6.

The perforated inner layer may serve as the layer that comes into direct contact with the skin of the limb. It is therefore beneficial for the perforated inner layer to be tacky. In this manner, the perforated inner layer helps to keep the liner in place on the limb and prevents slippage between the liner and limb.

The perforated inner layer may be any material suitable for use in a liner and which provides adequate distribution of perspiration formed by the limb into the porous layer while remaining in place on the limb. Various polymers may be used for the perforated inner layer. More specifically, an example of a material that may be used for the perforated inner layer is silicone. As a hydrophobic material, silicone is well suited for directing perspiration formed at the interface of the limb and the perforated inner layer towards the porous layer. Any of the materials suitable for use as the inner perforated layer, including silicone, may also be impermeable. An impermeable material will ensure that water forming at or around the perforated inner layer will flow not into the perforated inner layer, but rather will move towards and into the perforations and subsequently in to the porous layer.

Perforations in the perforated inner layer extend from one surface of the perforated inner layer to the opposing surface of the inner surface. In this configuration, portions of the skin of the limb will contact the perforated inner layer, while other portions of the skin of the limb are located over the perforations, thereby forming a space between the skin of the limb and the porous layer.

The perforations of the inner layer may be larger than the pores of the porous layer, so as to provide larger areas for the perspiration to collect before moving into the porous layer. Providing larger perforations also reduces the amount of perforated inner layer contacting the skin, thus making it more likely that perspiration forming on the limb will be over a perforation rather than between the perforated inner layer and the skin of the limb.

The outer layer may serve as the layer that comes into direct contact with a prosthesis. The material of the outer layer, like the material of the perforated inner layer, may be any material suitable for use in a liner. The material of the outer layer may be a material that provides additional beneficial characteristics to the sleeve, such as additional support to the structure of the liner or additional cushioning to increase the comfort of the user.

Various polymer materials may be used for the outer layer, such as, by example, a silicone-based material. Any of the materials of the outer layer may be permeable or impermeable. When permeable, the perspiration that has traveled from the limb through the porous layer can then pass through the outer layer to leave the liner. When impermeable, the perspiration travels from the limb through the porous layer and will be retained in the liner. In this configuration, the porous layer either retains the perspiration in order to keep liquid from collecting at the liner-limb interface or the liner will further comprise a means for expelling perspiration that collects between the porous layer and the outside layer, such as a drain.

Silicone material suitable for use in both the outer layer and perforated inner layer 22 is not limited, and may be the silicone elastomer material described in U.S. Pat. Nos. 6,592,539 and 6,136,039, both of which are owned by the assignee of the pending application.

B. The Second Embodiment

In another exemplary embodiment, the liner is formed as an elongate, closed-ended, generally conical base layer with a plurality of holes, wherein the holes are filled with a porous material and a perforated inner layer is located on the inner surface of the base layer.

As shown in FIGS. 5, 6, 7 and 8, the liner 40 has an elongate, closed-ended, generally conical shape for receiving a limb having roughly the same shape. The liner has a proximal end 42, which is open, and a distal end 44, which is closed. The liner 40 includes a base layer 46 with holes 52 located throughout the base layer 46, porous members 54 filled in the holes 52, and a perforated inner layer 56. The base layer 46 has an inside surface 48 and an outer surface 50 opposing the inner surface 48. The holes 52 extend from the inner surface 48 to the outer surface 50 of the base layer 46.

As is shown in FIGS. 5-9, the holes 52 are filled with porous members 54. The porous members 54 inserted in the holes 52 fill the holes 52 completely such that the surfaces of the porous members 54 at either side of the holes 52 are coplanar with the inner surface 48 and outer surface 50 of the base layer 46. The porous members 54 may be retained in the holes 52 of the base layer 46 by any variety of means, including an adhesive or by forming a tight fit between the porous member and the hole.

Figure 9:
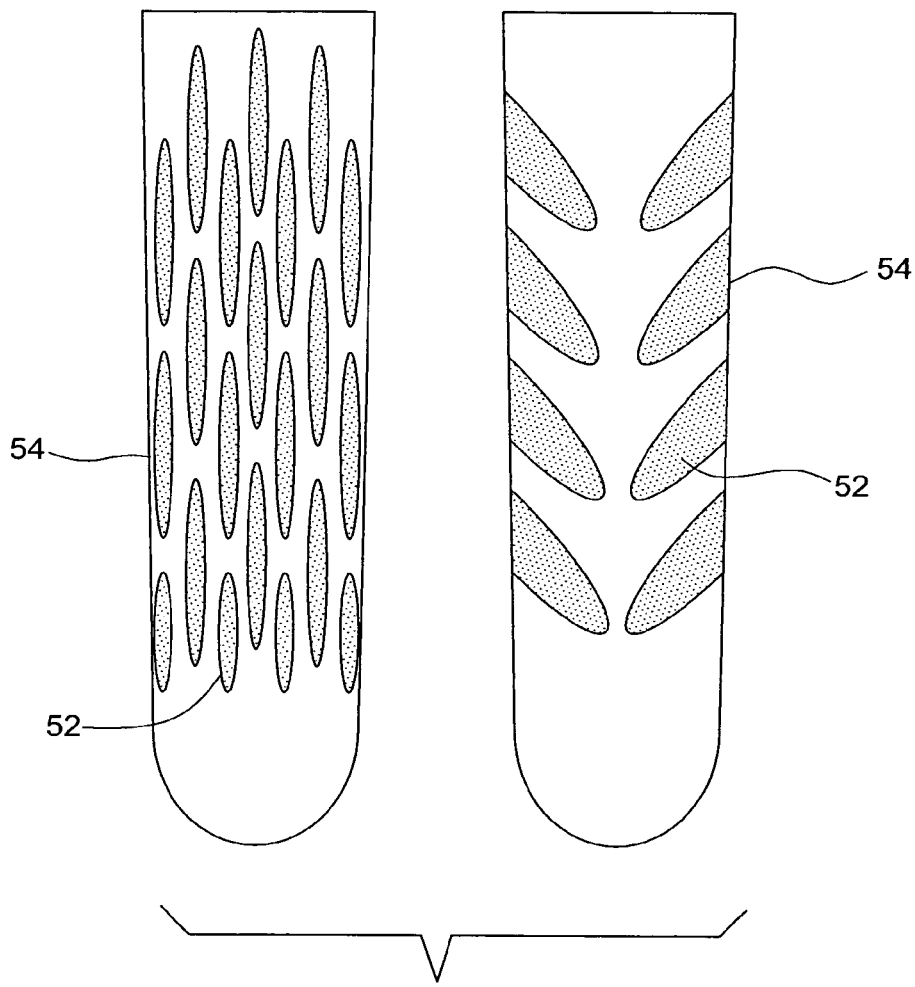
FIG. 9 is an elevational view of alternate forms of the liner depicted in FIG. 5.

FIG. 9 depicts two exemplary configurations for the holes. In one exemplary configuration, the holes 52 are vertically oriented ovals arranged in columns, wherein the holes of a column are offset from the holes of an adjacent column. In this configuration, no holes are formed in the distal area of the liner. Each of these holes is filled with a porous member 54. In a second exemplary configuration, the holes 52 have an oval shape and are aligned in columns. The holes are oriented at an approximately 45 degree angle, with each column being the mirror opposite of the adjacent column. In this configuration, no holes are formed at the distal end of the liner. A porous member 54 is located in each of these holes 52.

It will be noted that that the size, shape, location and pattern of the holes are not limited to those shown in FIG. 9, and may be any configuration suitable for use in a liner. The holes may be uniform in size and spaced in a consistent pattern, or the holes may vary in shape and be placed randomly about the liner. However, the holes should not be so large or so numerous as to destroy the structural integrity of the base layer.

The liner may further include a prosthesis attachment member, whether an outer layer is employed or not. The attachment mechanism may be formed in the distal area where no holes are formed. Any prosthesis attachment mechanism known in the art may be added to the liner, including, but not limited to, seal-in suspension, locking pin and vacuum with sleeve.

The thickness of the liner may be varied depending on such factors as the amount of cushioning desired by the user. With respect to the thickness of each layer of the liner, the thickness of the layers is limited only by the total thickness of the liner desired. The base layer may be thicker than the perforated inner layer. As noted above, the porous member will typically have the same thickness as the base layer so that the surfaces of the porous members are coplanar with the surfaces of the base layer.

The thickness of the base layer and porous members may be greater than the thickness of the perforated inner layer such that the porous members are capable of managing a large amount of perspiration. A porous layer with a greater thickness will have a greater capacity to store perspiration. A larger storage capacity allows the user to wear the liner for a longer period of time without the necessity to change or clean the liner. Such a configuration makes the liner especially useful when the desired function of the sleeve is to absorb and store perspiration rather than transport it out of the liner.

The overall size of the liner may be any size needed to fit the size of the limb of the user.

The porous members in accordance with this embodiment may be made from any of a number of porous materials capable of absorbing liquid and that are suitable for use in a liner. For example, the porous members may be a three-dimensional woven synthetic material, wherein the three-dimensional woven structure provides a network of pores, gaps and/or tunnels throughout the material in to which perspiration may travel. The three-dimensional woven structure is also such that these pores, gaps and/or tunnels are interconnected and provide a path from one surface of the porous member to the opposing surface.

The three-dimensional woven structure may be synthetic in order to increase the durability and longevity of the porous members as compared to natural materials. However, the material suitable for the porous members of the embodiment is not limited to synthetic materials where natural materials will achieve common functionality.

A specific example of material suitable for use as the porous material in the liner of the embodiment is made by TYTEX Group, Ikast, Denmark under product designation Quality No. 95289 and Tytex 5754/6.

The base layer may be any layer suitable for use in a liner. The base layer may be a polymer material, and preferably is made of silicone. The material may also be impermeable, which helps to guide the perspiration away from the base layer and towards the holes filled with porous members.

The perforated inner layer may serve as the layer that comes into direct contact with the skin of the limb. It is therefore beneficial for the perforated inner layer to be tacky for the same reasons discussed above in the first embodiment.

The perforated inner layer may be any material suitable for use in a liner and which provides adequate distribution of perspiration formed by the limb into the porous members while remaining in place on the limb. Various polymers may be used for the perforated inner layer. More specifically, an example of a material that may be used for the perforated inner layer is silicone.

As discussed above in the first embodiment, silicone is a hydrophobic material and is thus well suited for directing perspiration formed at the interface of the limb and the perforated inner layer towards the porous members. Also as discussed above, certain advantages are achieved if the material of the inner perforated layer is impermeable.

Perforations in the perforated inner layer extend from one surface of the perforated inner layer to the opposing surface of the inner surface. In this configuration, portions of the skin of the limb will contact the perforated inner layer, while other portions of the skin of the limb will be located over the perforations, forming a space between the skin of the limb and the porous members or base layer, depending on the location of the perforation.

The perforations of the perforated inner layer may be larger than the pores of the porous members, which will provide larger areas for the perspiration to collect before moving into the porous members. Providing larger perforations also reduces the amount of the perforated inner layer contacting the skin, thus making it more likely that perspiration forming on the limb will be over a perforation rather than between the perforated inner layer and the skin of the limb.

Perspiration formed in the areas of skin located over the perforations will be funneled directly to the porous members or base layer. In the event the perforation is located over the porous members, the perspiration will begin to move through the tunnels and gaps of the porous member and away from the limb. Additionally, perspiration formed in the areas where skin contacts the perforated inner layer will be directed towards the perforations. As with the previous embodiment, a perforated inner layer made from impermeable material and having rounded edges for the holes will also direct perspiration towards the porous members.

While not depicted in FIGS. 5-9, the liner of this embodiment may also comprise an outer layer located on the outer surface of the base layer. As described above with respect to the first embodiment, an outer layer may serve as the layer that comes into direct contact with a prosthesis. The layers of the liner may be adhered together by any means known in the art, such as through the use of an adhesive material or by lamination.

The material of an outer layer, like the material of the perforated inner layer, may be any material suitable for use in a liner. The material of an outer layer may be a material that provides additional beneficial characteristics to the sleeve, such as additional support to the structure of the liner or additional cushioning to increase the comfort of the user.

Various polymer materials may be used for an outer layer, and specifically, silicone may be used for an outer layer. As discussed in the first embodiment, permeable or impermeable material may be used to achieve different effects.

As described in the first embodiment, the optional outer layer may be located co-extensively with the base layer only the distal area of the liner.

Silicone material suitable for use in the base layer, the perforated inner layer and the optional outer layer is not limited, and may be the silicone elastomer material described in U.S. Pat. Nos. 6,592,539 and 6,136,039, both of which are owned by the assignee of the pending application.

C. The Third Embodiment

In still another exemplary embodiment, the liner is formed as an elongate, closed-ended, generally conical, porous foam layer having a coating of silicone on the outer and inner surfaces of the porous foam layer. The liner of this embodiment may further comprise a discrete portion of a moisture-absorbing material, such as a powder, located in a variety of locations about the liner.

Figures 10, 11:
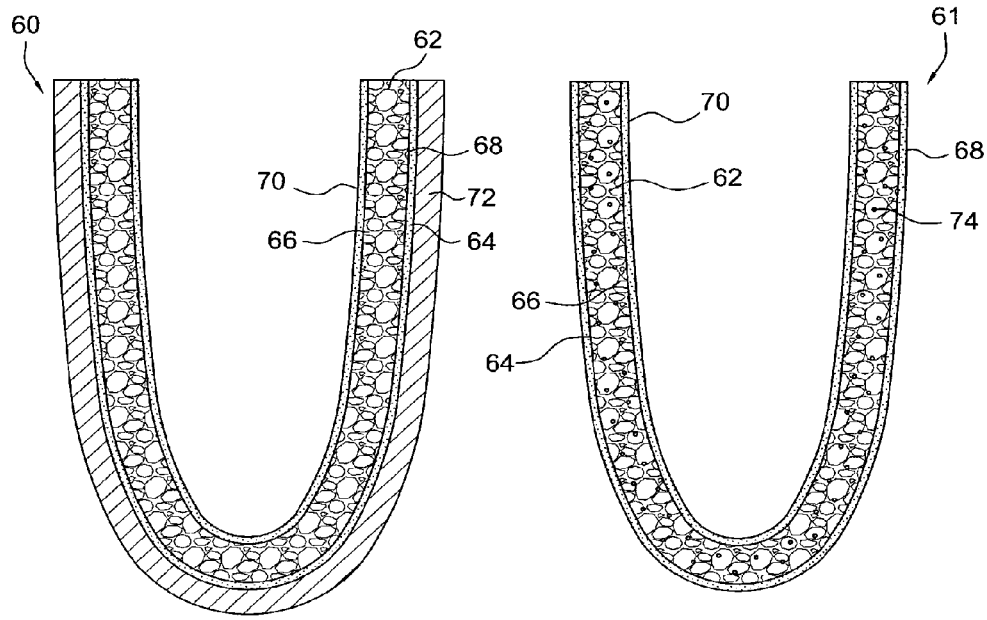
FIG. 10 is a vertical sectional view of still another embodiment of a liner.
FIG. 11 is a vertical sectional view of an alternate form of the embodiment depicted in FIG. 10.

As shown in FIG. 10, the liner 60 has an elongate, closed-ended, generally conical shape for receiving a limb having roughly the same shape. The liner has a proximal end, which is open, and a distal end, which is closed. The liner 60 includes a porous foam layer 62, an inner silicone coating 70 and an outer silicone coating 68 and an outer layer 72.

The porous foam layer 62 comprises an outer surface 64 and an inner surface 66 opposing the outer surface 64. The porous foam layer 62 further comprises a network of pores, gaps and/or tunnels that allow moisture to pass into one surface of the porous foam layer, such as the inner layer 66, and pass through the porous foam layer to the opposite surface, such as the outer surface 64. In this manner, the porous foam layer 62 is capable of absorbing perspiration that forms inside of the liner and transporting it to the outside of the liner, thus preventing the build up of liquid at the interface of the limb and the liner.

As also shown in FIG. 10, silicone layers 68, 70 may be formed on the inner surface 66 and outer surface 64 of porous foam layer 62. Inner silicone layer 70 is located on inner surface 66 of the porous foam layer 62 while the outer silicone layer 68 is formed on the outer surface 64 of the porous foam layer 62. The inner and outer silicone layers may be formed coextensively along the inner and outer surfaces of the porous foam layer. That is to say, the entire inner and outer surface of the porous foam layer is covered by the silicone layers.

As also shown in FIG. 10, the liner 60 may further comprise an outer layer 72 formed on the outer silicone layer 68.

The porous foam layer may be made from any foam material suitable for use in a liner and which has an ability to absorb and/or store moisture. The porous foam layer may be a porous polymer foam layer, and specifically, may be a porous silicone foam layer. This embodiment also contemplates using the open-cell silicone foam with hydrophilic particles as the porous foam layer disclosed in U.S. Provisional Application No. 60/858,371, filed Nov. 13, 2006, and U.S. patent application Ser. No. 11/979,758, which are both incorporated herein by reference.

The inner silicone layer and outer silicone layer may both be permeable and/or porous, such that the silicone layers allow for liquid in the form of perspiration to pass through the layers. In this manner, perspiration may pass into the liner through the inner layer; travel through the porous foam layer and out of the liner via the outer silicone layer to effectively keep perspiration formed by the limb from collecting at the interface of the limb and the liner.

The silicone layers may also be thinner than the porous foam layer so that perspiration travels easily through the layers into the porous foam layer and allowing for the porous foam layer to account for the bulk of the thickness of the liner. The more of the liner that is dedicated to the porous foam layer, the greater the capacity of the porous foam layer to store perspiration should the liner be designed to store excess perspiration.

The outer layer may be formed of any material suitable for use in the liner and the material for the outer layer will preferably be selected for its intended purpose. That is to say, if the outer layer is designed to add support to the liner, then the material should be more rigid. The layers of the liner may be adhered together by any means known in the art, such as through the use of an adhesive material or by lamination.

The outer layer may be a material such as a polymeric material, and more specifically may be silicone. As described in pervious embodiments, the material of the outer layer may also be either permeable of impermeable.

As shown in FIG. 11, a variation of a liner embodiment 61 includes discrete portions of a moisture-absorbing material 74 embedded within the porous foam layer 62.

The discrete portions of a moisture-absorbing material may be any material suitable for absorbing and storing perspiration and which may be embedded into foam. The discrete portions of the moisture-absorbing material work in concert with the porous foam layer, either providing additional means for absorbing and storing the perspiration or for absorbing and storing excess perspiration that the liner is not capable of moving out to the liner.

The amount of moisture-absorbing material embedded into the porous foam layer may also be varied depending on the demands of the user, with more moisture-absorbing material present when the liner is aimed at absorbing and storing perspiration rather than transporting it out of the liner.

Figures 12, 13:
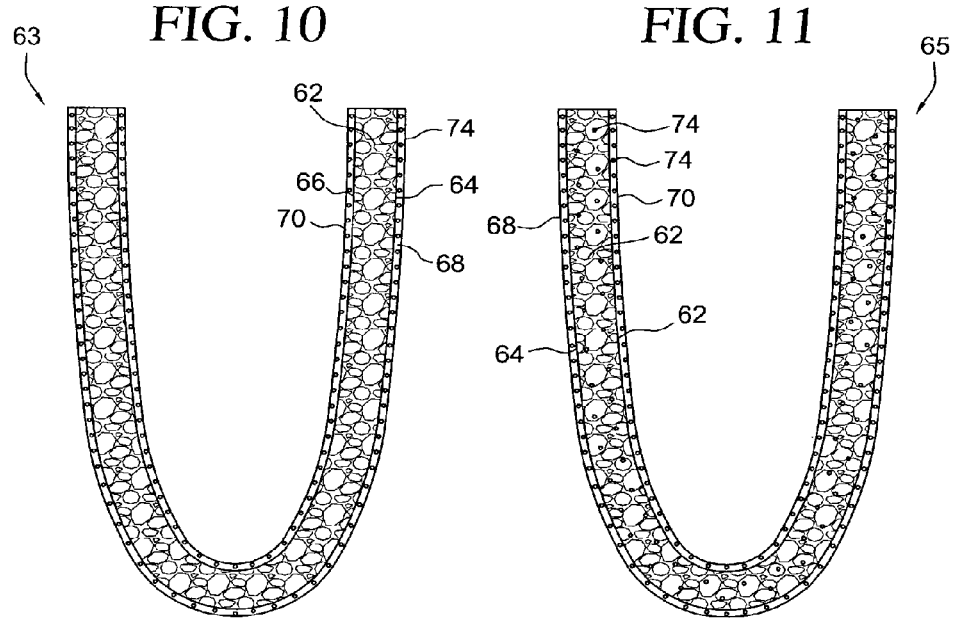
FIG. 12 is a vertical sectional view of an alternate form of the embodiment depicted in FIG. 10.
FIG. 13 is a vertical sectional view of an alternate form of the embodiment depicted in FIG. 10.

As shown in the liner variation 63 of FIG. 12, the moisture discrete portions of the moisture-absorbing material 74 may also be located between the silicone layers 68, 70 and the porous foam layer 62. In this manner, the portions of moisture-absorbing material 74 help to draw the moisture through the inner silicone layer 70 into the porous foam layer 62 at inner surface 66 and out of the porous foam layer 62 into the outer silicone layer 68 at the outer surface 64. As described above, any suitable moisture-absorbing material and form thereof may be used and the amount of the moisture-absorbing material 74 may vary based on the demands of the user and how the liner is to function.

As shown in another liner variation 65 in FIG. 13, the discrete portions of a moisture-absorbing material 74 are located both embedded within the porous foam layer 62 and between the silicone layers 68, 70 and within the porous foam layer 62 to draw on both of the attributes of the previously described variations of this embodiment.

The portions of moisture-absorbing material may be selected from any type and form capable of absorbing moisture and suitable for use in a liner, and the amount of moisture-absorbing material at either location may be varied depending on the demands of the user and the desired functionality of the liner.

As discussed above, each of the above variations of this embodiment may also be used when the porous foam layer is the material described in U.S. Provisional Application No. 60/858,371 and U.S. patent application Ser. No. 11/979,758. In such a configuration, the portions of moisture-absorbing material work in concert with the hydrophilic particles anchored to the pore walls of the porous material.

While the liner variations in FIGS. 11, 12 and 13, do not include an outer layer, each of the liners depicted are not prohibited from further including an outer layer should an outer layer be desired to provide additional beneficial characteristics to the liners, such as additional structural support.

D. The Fourth Embodiment

In another exemplary embodiment, the liner is formed as an elongate, closed-ended, generally conical polymer construct comprising multiple layers of polymer threads.

Figure 14:
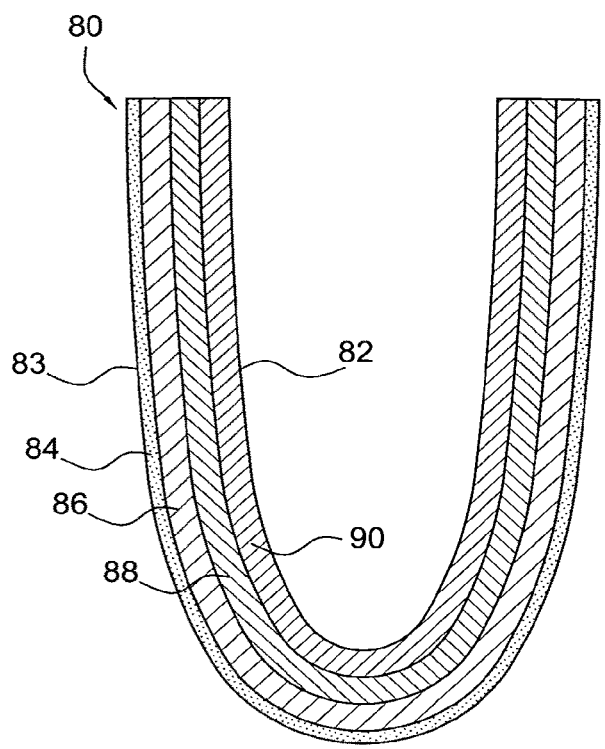
FIG. 14 is a vertical sectional view of yet another embodiment of a liner.

As shown in FIG. 14, the liner 80 has an elongate, closed-ended, generally conical shape for receiving a limb having roughly the same shape. The liner 80 has a proximal end, which is open, and a distal end, which is closed. The liner 80 includes multiple layers 84 wherein each layer is made from a plurality of aligned polymer threads.

As shown in FIG. 14, the liner has four layers 84, 86, 88, 90 of polymer threads. The layers 84 in the liner 80 may be at least two and there may be any number of layers of threads available while still exhibiting a thickness that is suitable for a liner. The inner surface 82 of the liner 80 may be in direct contact with the skin of the limb. Because the inner surface 82 of the liner 80 is the inner most layer of polymer threads, the polymer threads of this layer will be in direct contact with the skin of the limb. Accordingly, the inner most polymer thread layer may be tacky to help reduce slippage between the liner and the limb caused by perspiration forming at this interface.

Figure 15:
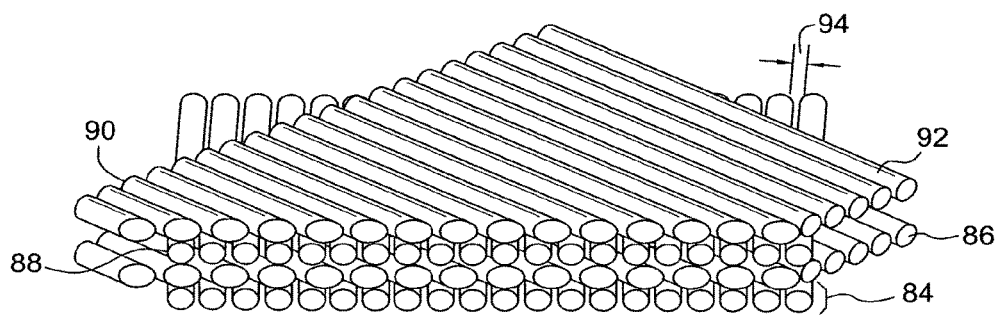
FIG. 15 is a detailed perspective view of the inner surface of the liner depicted in FIG. 14.

As shown in FIG. 15, each of the layers 84, 86, 88, 90 of polymer threads comprises a plurality of individual polymer threads 92 aligned in parallel. Also as shown in FIG. 15, each layer 84, 86, 88, 90 of polymer threads is aligned in the parallel to adjacent layers of polymer threads. However, polymer threads in separate layers are not aligned in parallel.

The polymer threads 92 may be generally arranged in a circular cross-section. However, the shape of the polymer threads is not limited to any specific geometric shape. The shape of the polymer threads may have cross sections in the shapes such as oval, pentagonal or hexagonal. The shape of the polymer threads should allow for gaps 94 to be created between polymer threads 92 in a layer and between adjacent layers 84, 86, 88, 90 of polymer threads. Such a configuration allows perspiration to travel through the layers of polymer threads via the gaps without being trapped within the plurality of layers.

The material of the polymer threads may be any suitable polymer for use in liners. As with previous embodiments, the polymer may be silicone. The silicone material is preferably impermeable, such that perspiration does not pass into the polymer threads but rather is directed towards the channels and gaps formed amongst the polymer threads and polymer thread layers.

The polymer threads of a layer may be oriented at an approximately 45 degree angle from the polymer threads of the adjacent layer. The degree at which each layer is offset is not limited and may be any degree of offset which maintains gaps between adjacent layers for perspiration to travel through.

The polymer threads and the layer of polymer threads may be adhered together by any means known in the art, such as through the use of an adhesive material or by lamination.

The size of the polymer threads is also not limited and may be any size suitable for use in a liner. Clearly, the cross section of the polymer threads may not be so big as to make the polymer threads impractical for use in a liner. Thus, the polymer threads should have a size such that several layers of stacked polymer threads are not thicker than the thickness of a traditional liner.

The shape and size of the polymer threads need not be the same for all polymer threads. That is to say, multiple shapes and sizes of polymer threads may be used both within a layer of polymer threads and amongst different layers of polymer threads. Again, so long as gaps and spaces are maintained in the liner for perspiration to travel through, the configuration is suitable for use in the liner disclosed herein. Thus, while FIG. 15 depicts polymer threads having the same circular shape and identical diameters, alternate configurations may have different shaped and sized polymer threads.

When the liner as described above is worn in direct contact with the skin of a limb, perspiration forming on the limb will be directed into the gaps and tunnels created between the polymer threads of each layer. The rounded edges of the polymer threads and use of an impermeable material for the polymer threads are two additional characteristics that will promote movement of perspiration into the gaps and tunnels.

The size of the gaps between polymer threads is not limited and may be any size that provides space between polymer threads for perspiration to travel. The objective is to allow space for perspiration to travel from the inner most layer of polymer threads to the outer most layer of polymer threads comprising the liner.

The gaps and tunnels amongst the polymer threads create a network that extends to the outer most surface of polymer threads making up the liner. Once perspiration has traveled through the network to the outer most surface of polymer threads, the perspiration exits the liner. Accordingly, the liner provides a means for managing perspiration formed on the limb and moving the perspiration out of the liner. In this manner, slippage between the liner and the limb due to accumulation of perspiration at the interface is avoided.

E. The Fifth Embodiment

In another exemplary embodiment, the liner comprises a polymeric construct comprising a plurality of packed polymeric balls.

Figure 16:
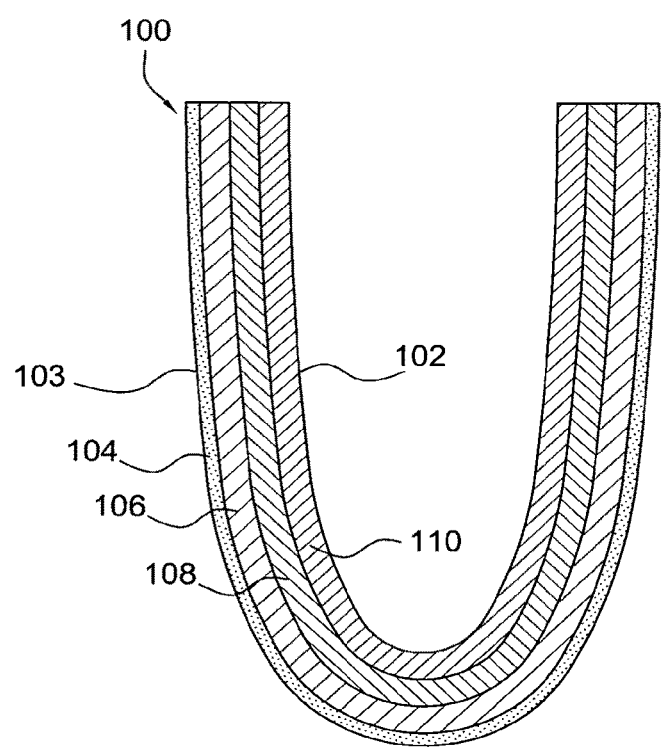
FIG. 16 is a vertical sectional view of still another embodiment of a liner.

As shown in FIG. 16, the liner 100 has an elongate, closed-ended, generally conical shape for receiving a limb having roughly the same shape. The liner 100 has a proximal end, which is open, and a distal end, which is closed. The liner 100 includes multiple layers 104, 106, 108, 110 wherein each layer is made from a plurality of packed polymeric balls. The number of layers in the liner may be at least two and may have any number of layers of balls possible while still having a thickness that is suitable for a liner.

The inner surface 102 of the liner 100 may be in direct contact with the skin of the limb. Because the inner surface 102 of the liner 100 is the inner most layer of polymeric balls, the polymer ball layer 110 will be in direct contact with the skin of the limb. Because of this, the inner most polymer ball layer may be tacky to help reduce slippage between the liner and the limb caused by perspiration forming at this interface.

Figure 17:
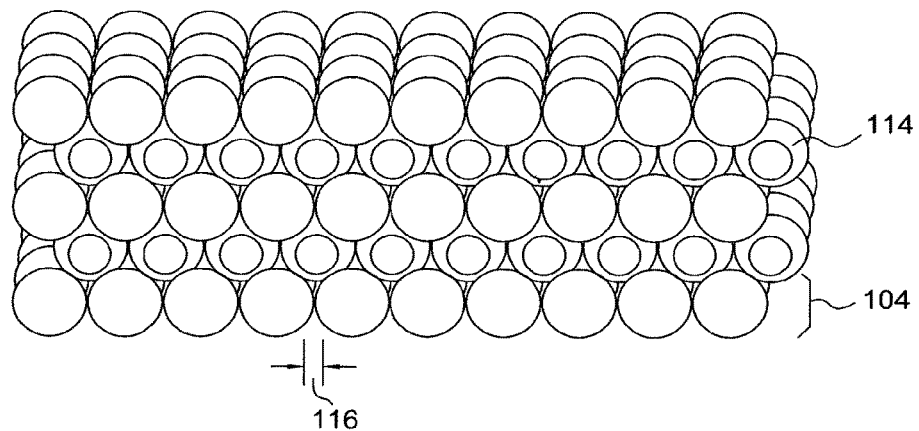
FIG. 17 is a detailed perspective view of the inner surface of the liner depicted in FIG. 16.

As shown in FIG. 17, each polymeric balls layer comprises a plurality of individual polymeric balls 114. The polymeric balls 114 in a layer may be configured such that all the balls touch adjacent balls. The polymeric ball layers may be stacked on top of each other such that each polymeric ball is directly on top of a polymeric ball in a lower layer, or, as shown in FIG. 17, the polymeric ball layers may be oriented such that the polymeric balls 114 of a layer are nestled into the space between adjoining balls of the lower polymeric ball layer. In either event, gaps 116 are maintained between the polymeric balls 114 and between the polymer ball layers such that a network of gaps and channels exists to allow perspiration to travel from the inner most layer to the outer most layer.

The material of the polymeric balls may be any suitable polymer for use in liners. As with previous embodiment, the polymer may be silicone. The silicone material is preferably impermeable, such that perspiration does not pass into the polymeric balls but rather is directed towards the channels and gaps formed amongst the polymeric balls and polymer ball layers.

The polymeric balls and the layer of polymeric balls may be adhered together by any means known in the art, such as through the use of an adhesive material or by lamination.

The shape of the polymeric balls is not limited to a perfect sphere. In other words, oval balls may also be used as well as any other three-dimensional shape that does not close off gaps between three-dimensional shapes and prevent perspiration from flowing through the network of gaps. While FIG. 17 shows the polymeric balls as having a spherical shape, the polymeric balls may also have other shapes, such as an oval shape. The shape of the polymeric balls should allow for gaps to be created between polymeric balls in a layer and between adjacent layers of polymeric balls. Such a configuration allows perspiration to travel through the layers of polymeric balls without being trapped within the plurality of layers.

The size of the gap between polymeric balls is not limited and may be any size that provides space between polymeric balls for perspiration to travel.

The size of the polymeric balls is also not limited and may be any size suitable for use in a liner. Clearly, the diameter of the polymeric balls may not be so big as to make the polymeric balls impractical for use in a liner. Thus, the polymeric balls should have a size such that several layers of stacked polymeric balls are not thicker than the thickness of a traditional liner.

The shape and size of the polymeric balls need not be the same for all polymeric balls. That is to say, multiple shapes and sizes of polymeric balls may be used both within a layer of polymeric balls and amongst different layers of polymeric balls. Again, so long as gaps and spaces are maintained in the liner for perspiration to travel through, the configuration is suitable for use in the liner disclosed herein. Thus, while FIG. 17 depicts polymeric balls having the same spherical shape and identical diameters, alternate configurations may have different shaped and sized polymeric balls.

When the liner as described above is worn in direct contact with the skin of a limb, perspiration forming on the limb will be directed into the gaps and tunnels created between the polymeric balls of each layer. The rounded edges of the polymeric balls and use of an impermeable material are two additional characteristics that will promote movement of perspiration into the gaps and tunnels.

As seen in FIGS. 14 and 16, the liners do not include an outer layer. However, the liners depicted in FIGS. 14 and 16 are not prohibited from further including an outer layer should the outer layer be desired to provide additional beneficial characteristics to the liners such as structural support. The characteristics and materials for such an outer layer are similar to those described above with respect to earlier embodiments.

The disclosed embodiments of a liner provide improved management of perspiration formed by a limb and consequently an improved liner that is less likely to slip on the limb and cause skin irritation to the limb.

It is understood that the size of the liners can be adjusted so that different users having different sized limbs may benefit from the present design.

Of course, it is to be understood that not necessarily all objects or advantages may be achieved in accordance with any particular embodiment described herein. Thus, for example, those skilled in the art will recognize that the invention may be embodied or carried out in a manner that achieves or optimizes one advantage or group of advantages as taught herein without necessarily achieving other objects or advantages as may be taught or suggested herein.

The skilled artisan will recognize the interchangeability of various features from different embodiments. In addition to the variations described herein, other known equivalents for each feature can be mixed and matched by one of ordinary skill in this art to construct a liner in accordance with principles of the present invention.

Although this invention has been disclosed in the context of certain exemplary embodiments and examples, it therefore will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

The invention claimed is:

1. A prosthetic liner in the shape of an elongated, generally conical sleeve having a closed distal end and an open proximal end for receiving a limb of a wearer, the liner defining an outer surface and an inner surface opposite the outer surface and spaced apart by a total thickness, the liner comprising:
    a tubular inner layer formed from a hydrophobic elastomer material and defining the inner surface of the liner adapted to come into direct contact with skin of the limb, the material of the inner layer having skin tackiness properties arranged to maintain the liner on the limb and prevent slippage between the liner and the limb of the wearer, the inner layer defining a plurality of perforations extending through the thickness of the inner layer and rounded edges about the perforations;
    a tubular porous layer laminated to the inner layer and defining a plurality of interconnected pores, the perforations of the inner layer extending over the pores of the porous layer such that skin of the limb will contact the perforated inner layer and extend over the porous layer at the perforations so as to form a space between the skin of the limb and the porous layer, the perforations of the inner layer being larger than the pores of the porous layer to provide larger areas for perspiration to collect before moving into the porous layer, the porous layer continuously extending along the inner layer, the porous layer constructed from a three-dimensional woven synthetic material;

a tubular outer layer laminated to the porous layer and adapted for cushioning, the outer layer extending along the entirety of the porous layer and having greater rigidity than the porous layer, the outer layer defining a plurality of holes exposing the porous layer, wherein the porous layer channels moisture from the inner surface to the outer surface through the plurality of holes of the porous layer, and a prosthesis attachment mechanism located on the outer layer;

wherein the thickness of the porous layer is greater than a combined thickness of the inner and outer layers such that more of the total thickness of the liner is defined by the porous layer than the inner and outer layers to facilitate travel of perspiration away from the limb;

wherein the inner layer is located along the entirety of the inner surface of the liner;

wherein the outer layer extends over the entirety of the outer surface of the liner;

wherein both the tubular outer layer and the tubular inner layer are formed from a silicone elastomer;

wherein the outer layer is closed-ended at the distal end of the liner and is devoid of any openings, holes, or apertures at said distal end; and wherein the prosthetic liner comprises substantially the same shape of the limb of the wearer.

2. The liner according to claim 1, wherein the outer layer is liquid and vapor impervious.

3. The liner according to claim 1, wherein the total thickness of the liner consists the thicknesses of the inner, porous and outer layers.

4. The liner according to claim 1, wherein the porous layer is a polymeric-based foam.

5. The liner according to claim 4, wherein the porous layer includes discrete portions of a moisture-absorbing material.

6. The liner according to claim 5, wherein the porous layer is generally hydrophobic.

7. The liner according to claim 1, wherein the inner layer is directly laminated to the porous layer thereby forming a laminate structure.

8. The liner according to claim 1, wherein the porous layer is directly joined to the outer layer.

9. The liner according to claim 1, wherein the porous layer includes a plurality of polymeric threads arranged in a parallel configuration.

10. The liner according to claim 1, wherein the porous layer includes discrete portions of a moisture-absorbing material.

11. The liner according to claim 1, wherein the inner layer is moisture and vapor impervious.

12. The liner according to claim 1, wherein surfaces of the porous layer are coplanar with an inner surface of the outer layer.

13. The liner according to claim 1, wherein the outer layer is laminated onto the porous layer such that the inner layer, the porous layer and the outer layer form a tri-layered laminate structure.

14. The liner according to claim 1, wherein the holes of the outer layer are spaced apart by solid areas of the outer layer having a thickness extending from the inner layer to the outer surface of the liner.

* * * * *